(12) United States Patent
Nathan

(10) Patent No.: US 12,350,454 B2
(45) Date of Patent: Jul. 8, 2025

(54) LIMA CROSSOVER INTEGRATED CATHETER SYSTEM

(71) Applicant: THE UNIVERSITY OF CHICAGO, Chicago, IL (US)

(72) Inventor: Sandeep Nathan, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1104 days.

(21) Appl. No.: 17/250,957

(22) PCT Filed: Oct. 4, 2019

(86) PCT No.: PCT/US2019/054683
§ 371 (c)(1),
(2) Date: Apr. 1, 2021

(87) PCT Pub. No.: WO2020/072895
PCT Pub. Date: Apr. 9, 2020

(65) Prior Publication Data
US 2021/0346654 A1     Nov. 11, 2021

Related U.S. Application Data

(60) Provisional application No. 62/876,928, filed on Jul. 22, 2019, provisional application No. 62/740,957, filed on Oct. 4, 2018.

(51) Int. Cl.
*A61M 25/09*     (2006.01)
*A61M 25/00*     (2006.01)
*A61M 25/01*     (2006.01)

(52) U.S. Cl.
CPC ........ *A61M 25/09* (2013.01); *A61M 25/0021* (2013.01); *A61M 2025/0175* (2013.01); *A61M 2210/127* (2013.01)

(58) Field of Classification Search
CPC .............. A61M 25/09; A61M 25/0021; A61M 2025/0175; A61M 2210/127;
(Continued)

(56) References Cited

U.S. PATENT DOCUMENTS

| 4,909,258 A | 3/1990 | Kuntz et al. |
| 2004/0019359 A1* | 1/2004 | Worley ............. A61M 25/0041 600/585 |

(Continued)

OTHER PUBLICATIONS

Zaheed Tai, Selective LIMA Injection Via the Right Radial Approach, Jan./Feb. 2011, Cardiac Interventions Today, pp. 1-2 (Year: 2011).*
(Continued)

*Primary Examiner* — Theodore J Stigell
(74) *Attorney, Agent, or Firm* — Norton Rose Fulbright US LLP

(57) ABSTRACT

The present disclosure includes an integrated catheter system for cannulation of a LIMA graft from a right radial access point. Some integrated catheter systems include a guide catheter comprising an elongated member having an outer sheath body portion that includes an outer sheath proximal end, an outer sheath distal end, and an outer sheath lumen extending through the outer sheath between the outer sheath proximal end and the outer sheath distal end, the outer sheath including a curved section that includes: a first curved segment, a second curved segment, a third curved segment, a fourth curved segment, a first extended segment between the third curved segment and the fourth curved segment, and a second extended segment between the fourth curved segment and the outer sheath distal end.

17 Claims, 12 Drawing Sheets

(58) Field of Classification Search
CPC ........ A61M 2025/0004; A61M 31/005; A61M 25/0041; A61M 25/01
See application file for complete search history.

(56) References Cited

U.S. PATENT DOCUMENTS

| | | |
|---|---|---|
| 2004/0044350 A1 | 3/2004 | Martin et al. |
| 2007/0106260 A1* | 5/2007 | Ishii .................. A61M 25/0021 604/523 |
| 2007/0249997 A1 | 10/2007 | Goodson et al. |
| 2008/0183259 A1* | 7/2008 | Bly ........................ A61N 1/057 607/118 |
| 2016/0317788 A1 | 11/2016 | Merkel |
| 2017/0266415 A1 | 9/2017 | Lampropoulos et al. |
| 2018/0132837 A1 | 5/2018 | Mathena et al. |

OTHER PUBLICATIONS

Tai, "Selective LIMA Injection Via Right Radial Approach", Cardiac Interventions Today, p. 31-32, (Jan./Feb. 2011).*
International Search Report and Written Opinon issued in Corresponding PCT Application No. PCT/US2019/054683, dated Dec. 17, 2019.

* cited by examiner

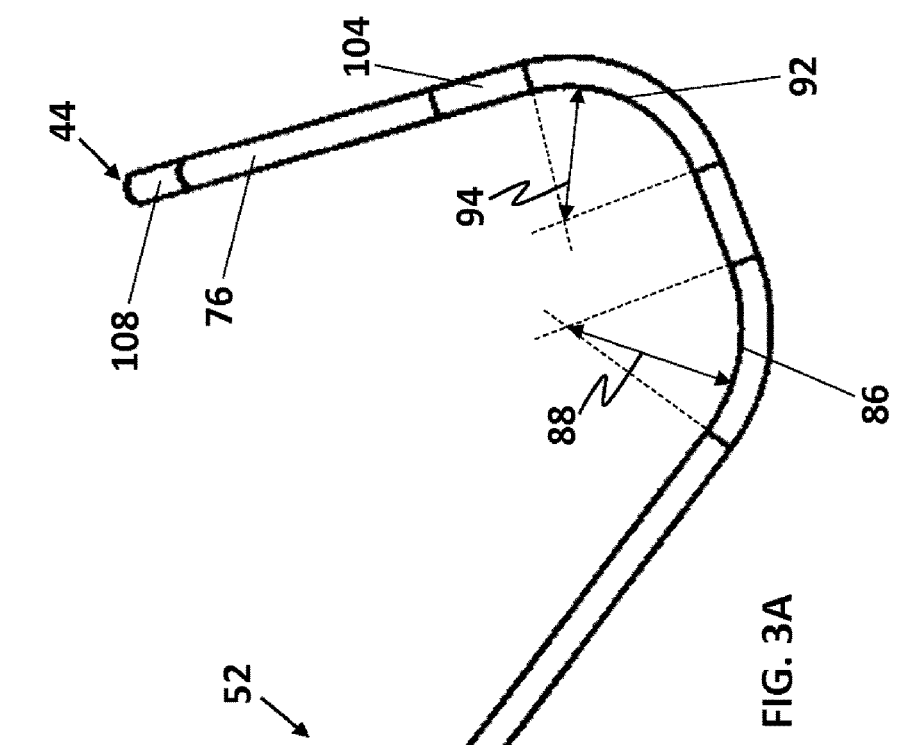
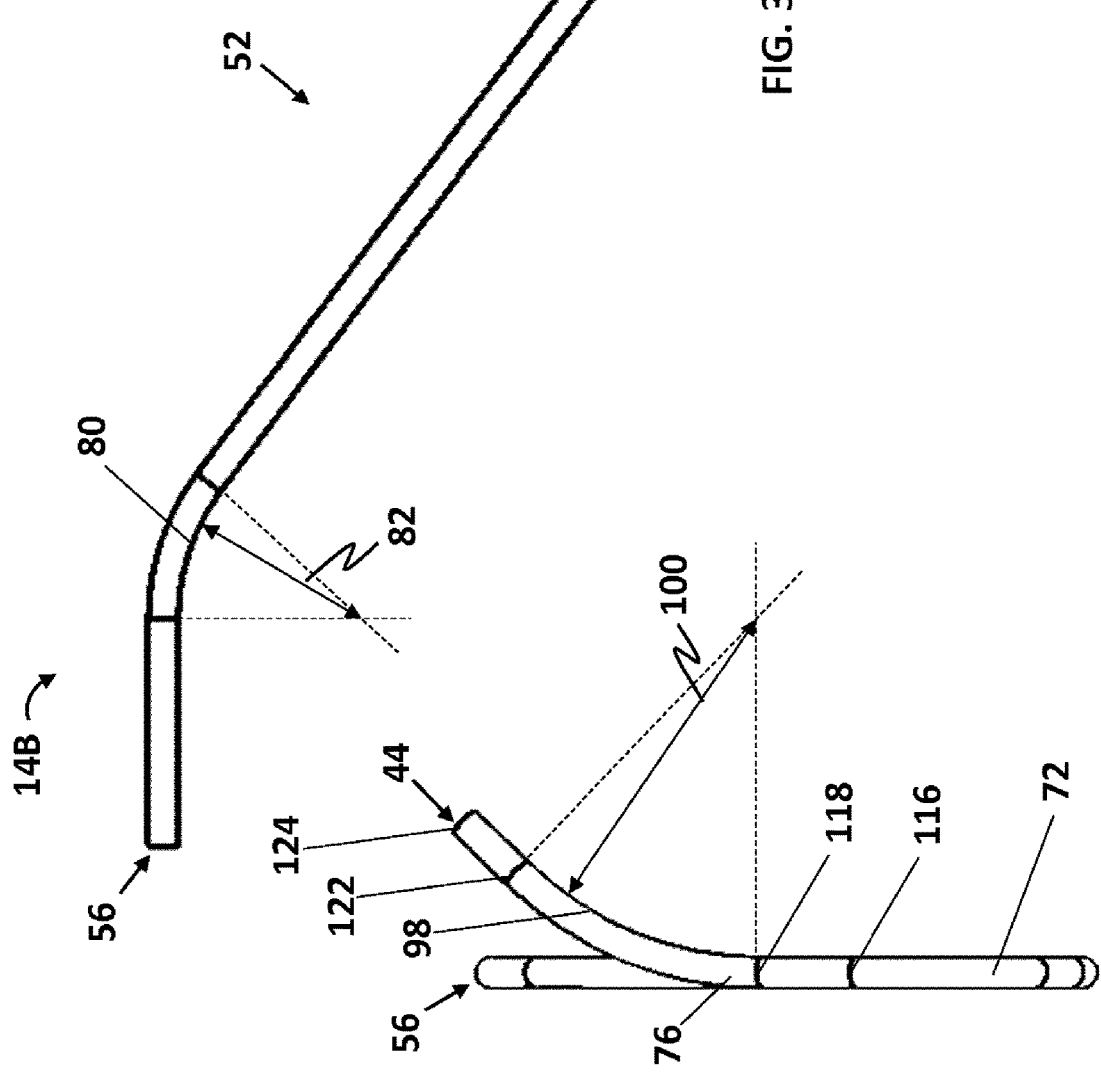
FIG. 3A
FIG. 3B

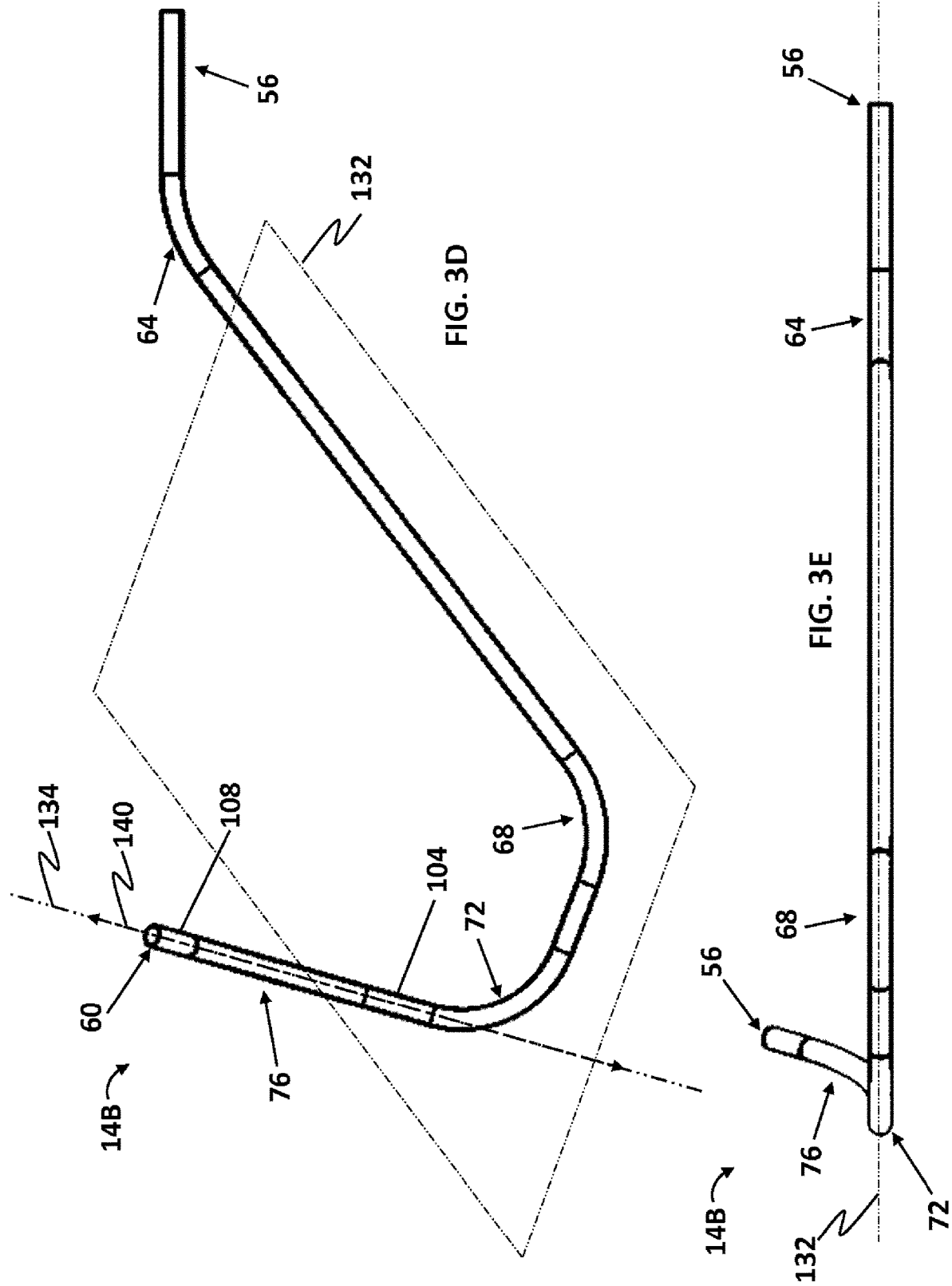

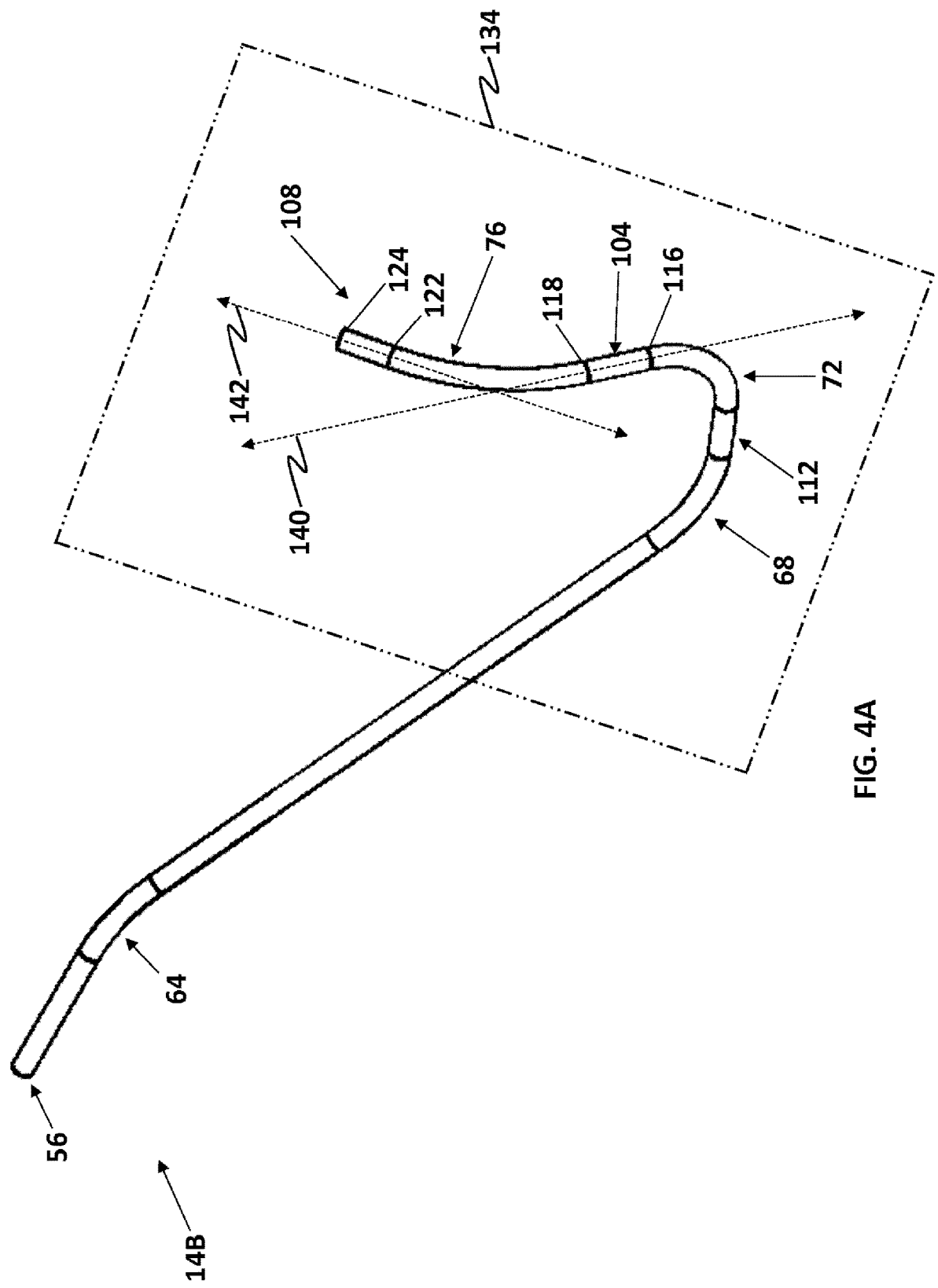

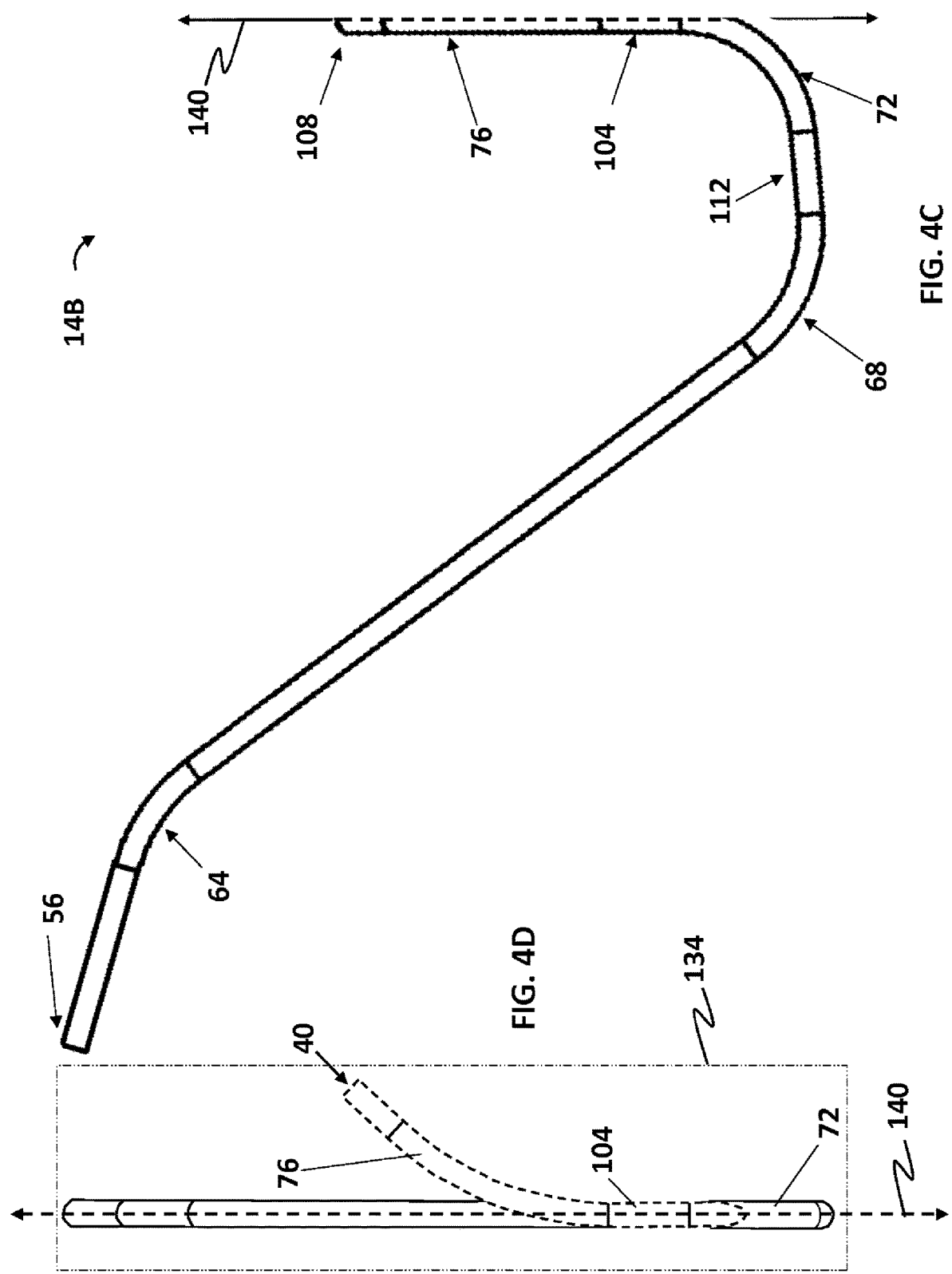

LIMA CROSSOVER INTEGRATED CATHETER SYSTEM

CROSS-REFERENCE TO RELATED APPLICATIONS

This application is a national phase application under 35 U.S.C. § 371 of International Application No. PCT/US2019/054683, filed Oct. 4, 2019, which claims the benefit of priority of U.S. Provisional Patent Application No. 62/740,957 filed Oct. 4, 2018, and U.S. Provisional Patent Application No. 62/876,928 filed Jul. 22, 2019, all of which are hereby incorporated by reference in their entirety.

FIELD OF INVENTION

The present invention relates generally to apparatuses and methods of using cardiac catherers; and more specifically, but not by way of limitation, to cardiac catheters for angiographic procedures of a left internal mammary artery bypass graft performed using a right radial arterial approach.

BACKGROUND

Coronary heart disease ("CHD") is a disease where plaque builds up inside the coronary arteries, which supply oxygen-rich blood to your heart. Over time, this plaque can harden or rupture reducing the flow of blood to the heart. Reduced, or completely blocked, blood flow in the coronary arteries will often lead to a heart attack. Coronary artery bypass graft ("CABG") is a is a type of surgery that improves blood flow to the heart by using a healthy artery or vein from the body to bypasses the blocked portion of the coronary artery. Pedicled left internal mammary artery ("LIMA") bypass grafts are commonly created in the context of CABG surgery and are most often anastomosed to the Left Anterior Descending ("LAD") coronary artery. The LIMA arises from the left subclavian artery (LSCA), projects slightly anterior to the axis of the LSCA, and courses downward into the thoracic cavity.

Millions of patients have patent LIMA grafts which will need angiographic surveillance, or cardiac catheterization, in the future. Engagement of the LIMA graft usually requires catheterization from either the left radial approach or from the transfemoral approach because a right transradial approach, while safer for patients than a transfemoral approach, is also far more technically challenging due to multiple angles and contact points in the vasculature and limited torque response, prompting operators to abandon the right radial approach in favor of other, less familiar, vascular access points.

LIMA cannulation from the right radial is technically challenging and has a learning curve. Presently, a right transradial approach is typically only considered in circumstances when the left radial artery has been explanted as a bypass graft or the right internal mammary artery (RIMA) has been used for bypass. A limited number of options currently exist for LIMA catheterization from a right transradial approach. One known method is the use of standard catheters (e.g., Right/Left Coronary Bypass, Judkins, or Tiger catheter) to direct a catheter into the descending thoracic aorta, facing the superior wall of the arch, and engaging the LSCA, after which the catheter is exchanged over a long guidewire for a separate catheter (e.g., IM, RIM, or Cobra catheters) to engage the LIMA. Often multiple catheter selections must be tried before a suitable catheter curve is discovered to comply with the particular aortic geometry of a patient. Currently there is no uniform approach to complete catheterization of the LIMA from the right transradial approach in a safe and efficient manner. Thus, there exists a need for a catheter shaped to facilitate efficient cannulation of the (LIMA) graft from the ergonomically more favorable right radial approach.

SUMMARY

The present disclosure describes an integrated two-part catheter system that facilitates a uniform approach for efficient cannulation of a LIMA graft from a right radial access point, the vascular access site of choice by the majority of transradial operators, with the ability to function with various aortic arch geometries. Some configurations of the apparatus can facilitate efficient cannulation of left internal mammary artery (LIMA) graft from the ergonomically more favorable right radial approach by comprising a catheter system that integrates a deliberately shaped, guide catheter designed to engage the LSCA from a right transradial approach, with an integrated telescoping catheter, shaped to engage the LIMA ostium. In some configurations, such advantageous catheter systems can be achieved by using a delivery system delivery system comprising an outer sheath including an elongated member having an outer sheath body portion that includes an outer sheath proximal end, an outer sheath distal end opposite from the outer sheath proximal end, and an outer sheath lumen extending through the outer sheath between the outer sheath proximal end and the outer sheath distal end, the outer sheath including a curved section that is nearer the outer sheath distal end than the outer sheath proximal end. In some configurations, a default shape of the curved section includes, from a proximal portion of the curved section and extending toward a distal portion of the curved section: a first curved segment having a first curve with a first radius of curvature; a second curved segment with a second curve having a second radius of curvature, the curvature of the second curved segment in a different direction than the curvature of the first curve; a third curved segment with a third curve having a third radius of curvature that is smaller than each of the first and second radii of curvature, the curvature of the third curved segment in a common direction as the curvature of the second curve; a fourth curved segment with a fourth curve having a fourth radius of curvature that is smaller than each of the first and second radii of curvature; a first extended segment between the third curved segment and the fourth curved segment, the first extended segment being axial or having a curve with a radius of curvature that is larger than the second radius of curvature; and a second extended segment between the fourth curved segment and the outer sheath distal end, the second extended segment being axial or having a curve with a radius of curvature that is larger than the second radius of curvature. In some configurations, the third curved segment is disposed in a first plane, and the fourth curved segment is disposed in a second plane that is rotated relative to the first plane around an axis that extends through the center of the outer sheath lumen at proximal and distal ends of the first extended segment.

In some such configurations, the second extended segment extends laterally relative to the third and fourth curved segments. In some configurations, a portion of the outer sheath, viewed from the perspective of the outer sheath distal end facing toward the outer sheath proximal end, defines a spiral that curves in a counter-clockwise direction. In some of the foregoing configurations, the outer sheath has a length of between 85 and 95 centimeters (cm). In some configurations, the outer sheath has a length that is greater than 85 cm, while in other configurations, the outer sheath has a length that is less than 85 cm. In some configurations, the outer sheath has an outer diameter corresponding to 6 French gauge or 5 French gauge.

In some configurations, the delivery system further comprises an inner sheath comprising an elongated member having an inner sheath body portion that includes an inner sheath proximal end, an inner sheath distal end opposite from the inner sheath proximal end, and an inner sheath lumen extending through the inner sheath between the inner sheath proximal end and the inner sheath distal end, the inner sheath including a curved section that is nearer the inner sheath distal end than the inner sheath proximal end. In some such configurations, a default shape of the curved section includes, from a proximal portion of the curved section and extending toward a distal portion of the curved section: a first curved segment having a first radius of curvature; a first extended segment between the first curved segment and the inner sheath distal end, the extended segment being axial or having a curve with a radius of curvature that is larger than the first radius of curvature. In some configurations, the curved segment is of sufficient length relative to the first radius of curvature that the first extended segment extends in a direction toward a plane that is interested by and perpendicular to a portion of the inner sheath that is closer to the inner sheath proximal end than to the inner sheath distal end. In some configurations, the inner sheath is configured to extend through the outer sheath proximal, the outer sheath lumen, and the outer sheath distal end.

In some of the foregoing configurations, the inner sheath has an outer diameter corresponding to 4 French gauge or 5 French gauge. In some configurations, a length of the inner sheath is greater than a length of the outer sheath lumen. In some configurations, the delivery system is configured to enable access to a patient's left internal mammary artery (LIMA) via a right transradial approach. In some configurations, a portion of the outer sheath, viewed from the perspective of the outer sheath distal end facing toward the outer sheath proximal end, defines a spiral that curves in a clockwise direction.

Some of the configurations comprise, a method for accessing the left internal mammary artery from a right transradial approach. Some such methods comprise inserting a guide member into a blood vessel of a patient. In some such configurations, the guide member comprises a curved section that includes, from a proximal portion of the curved section and extending toward a distal portion of the curved section: a first curved segment having a first curve with a first radius of curvature; a second curved segment with a second curve having a second radius of curvature, the curvature of the second curved segment in a different direction than the curvature of the first curve; a third curved segment with a third curve having a third radius of curvature that is smaller than each of the first and second radii of curvature, the curvature of the third curved segment in a common direction as the curvature of the second curve; a fourth curved segment with a fourth curve having a fourth radius of curvature that is smaller than each of the first and second radii of curvature; a first extended segment between the third curved segment and the fourth curved segment, the first extended segment being axial; and a second extended segment between the fourth curved segment and the outer sheath distal end, the second extended segment being axial; where the third curved segment is disposed in a first plane, and the fourth curved segment is disposed in a second plane that is rotated relative to the first plane around an axis that extends through the center of an outer sheath lumen at proximal and distal ends of the first extended segment.

Some methods comprise the step of navigating the guide member through the right subclavian artery into the descending aorta of the aortic arch, engaging the left subclavian artery ostium with the distal end of the guide member, telescoping an inner sheath through a lumen of the guide member, and engaging the left internal mammary artery with a distal end of the inner sheath. In some methods, inserting the guide member into a patient's blood vessel comprises inserting the outer sheath into the radial artery of the patient. In some configurations, the inner sheath comprises a curved section that includes a fifth curved segment having a fifth radius of curvature and a third extended segment between the fifth curved segment and an inner sheath distal end, the third extended segment being axial, where the fifth curved segment is of sufficient length relative to the first radius of curvature that the third extended segment extends in a direction toward a plane that is interested by and perpendicular to a portion of the inner sheath that is closer to an inner sheath proximal end than to the inner sheath distal end.

In some methods, engaging the left subclavian artery ostium with a distal end of the guide member comprises rotating the distal end of the guide member so that the second extended segment is coaxial with a portion of the left subclavian artery. In some methods, navigating the guide member comprises positioning the second curved segment, the third curved segment, and the fourth curved segment of the guide member into the descending aorta and positioning the first curved segment of the guide member in the right subclavian artery. In some configurations, engaging the left internal mammary artery with a distal end of the inner sheath does not comprise using a guide wire to exchange the guide member.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed configuration, the term "substantially" may be substituted with "within [a percentage] of" what is specified, where the percentage includes 0.1, 1, 5, and 10 percent.

Further, an apparatus or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any configuration of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one configuration may be applied to other configurations, even though not described or illustrated, unless expressly prohibited by this disclosure or the nature of the configurations.

Some details associated with the configurations described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 3A-3B are front and right views, respectively, of a curved section of a second configuration of an outer guide of the present apparatuses.

FIGS. 3D-3E are rear and bottom views, respectively, of the curved section of the second configuration of the outer guide.

FIGS. 4A-4B are perspective views of the curved section of the second configuration of the outer guide FIGS. 4C-4D are cutaway views of the curved section of the second configuration of the outer guide.

DETAILED DESCRIPTION

Figure 1:
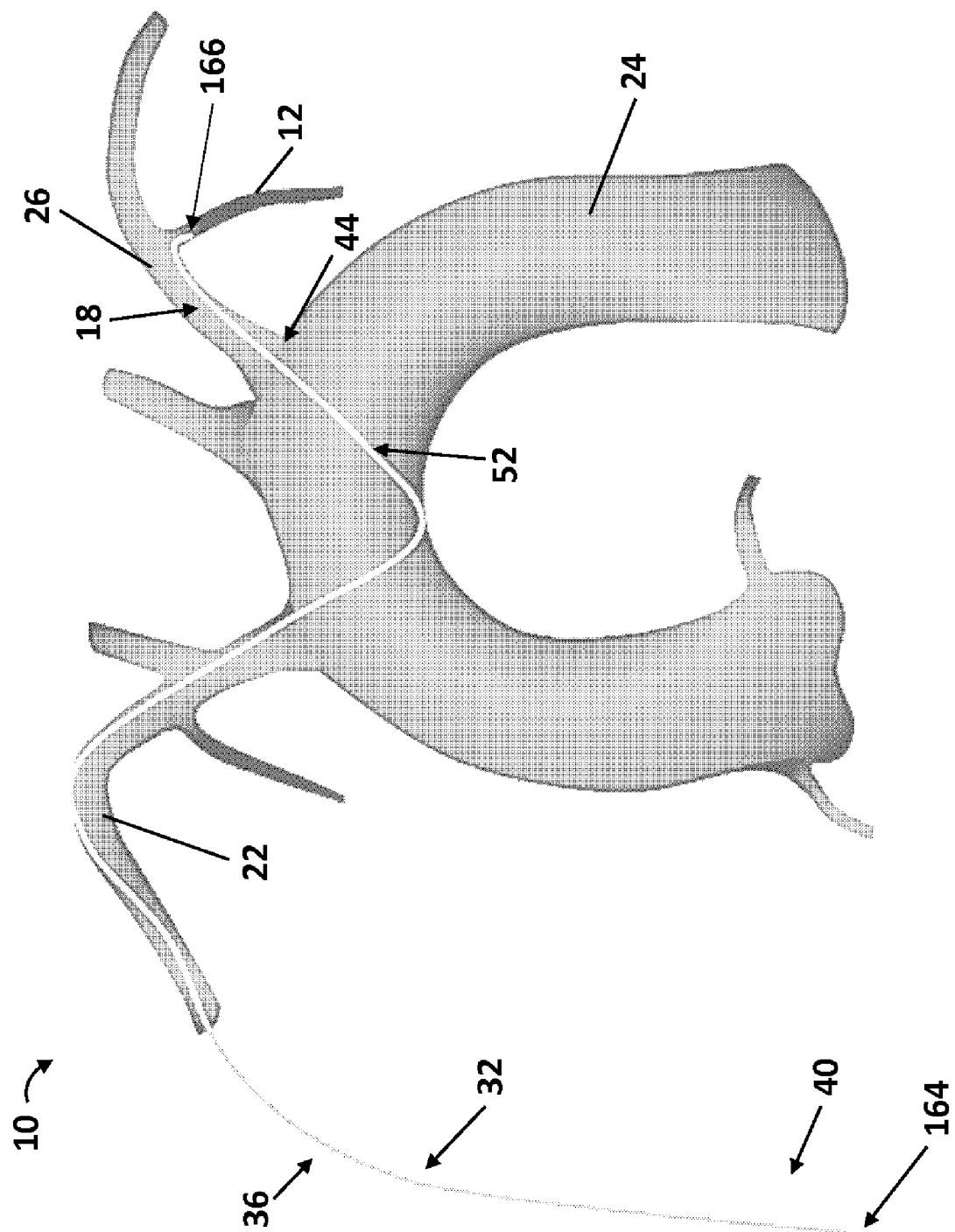
FIG. 1 is a schematic view of a first example of the present apparatuses, shown in use engaging the ostium of the LIMA from a right transradial approach.

Referring now to the drawings, and more particularly to FIG. 1, shown therein and designated by the reference numeral 10 is a first example of the present apparatuses. In the depicted configuration, apparatus 10 is a guide system. Guide system 10 may be employed as a catheter during a cardiac catheterization procedure, such as, angioplasty, angiography, balloon septostomy, balloon sinuplasty, cardiac electrophysiology testing, or catheter ablation.

In the configuration shown in FIG. 1, guide system 10 is shown as a delivery system for accessing a blood vessel in a cardiac catheterization procedure, for example angiographic surveillance of the left interior left internal mammary artery ("LIMA") 12 bypass graft using the right transradial approach (as illustrated in FIG. 1). In the depicted configuration, guide system 10 comprises an outer sheath 14 and an inner sheath 18. In the depicted configuration, inner sheath 18 is disposed within outer sheath 14 to facilitate a uniform approach for cannulation of a LIMA 22 graft from a right radial access point with the ability to function with various aortic arch geometries.

Outer sheath 14 and/or inner sheath 18 may each be formed of a single continuous piece of material and can be shaped or formed by any of various known methods including, but not limited to, extrusion, molding, thermosetting, casting, machining, pressing and/or the like. In some configurations, outer sheath 14 and inner sheath 18 may comprise a flexible material. Outer sheath 14 and inner sheath 18 may comprise any of various known biocompatible polymers such as a suitable polymide and/or polymer, including, but not limited to, silicone rubber, nylon, polyurethane, polyethylene terephthalate (PET), latex, and thermoplastic elastomers.

As shown in FIG. 1, guide system 10 may be formed such that when positioned into a blood vessel of a patient via a right transradial approach, outer sheath 14 may navigate through the right subclavian ("RSA") 22 and aortic arch 24 to engage the left subclavian artery ("LSA") 26, and inner sheath 18 may telescope through outer sheath 14 to extend beyond the distal end of outer sheath 14 to engage the LIMA 12.

In guide system 10, outer sheath 14 is configured to engage LSA such that outer sheath distal end 44 is positioned within the LSA ostium to allow sufficient clearance for inner sheath 18 to engage LIMA without a guide wire or catheter exchange. This allows for a more efficient and uniform approach than allowed by current catheters, which may require parking a catheter in LSA 26 and then advancing a deep guide wire into the subclavian artery and exchanging a different catheter over the wire in order to engage the LIMA.

In the example depicted in FIG. 1, outer sheath 14 comprises an elongated member 32 having an outer sheath body portion 36 that includes an outer sheath proximal end 40 and an outer sheath distal end 44 opposite from the outer sheath proximal end, and an outer sheath lumen 48 extending through the outer sheath between the outer sheath proximal end and the outer sheath distal end. Outer sheath distal end 44 may be coupled to various instruments, such as a balloon, stent, or other instruments known in the art. Outer sheath proximal end 40 may be coupled to a controller, machine, intravenous fluid, contrast dye, tool, or other instrument.

As shown in FIG. 1, outer sheath 14 includes a curved section 52. In some configurations, curved section 52 may be positioned nearer to outer sheath distal end 44 than to outer sheath proximal end 40. In other configurations, curved section 52 may comprise any section of outer sheath 14 between outer sheath distal end 44 and outer sheath proximal end 40. For example, curved section 52 may comprise a majority of outer sheath 10.

Figure 2A:
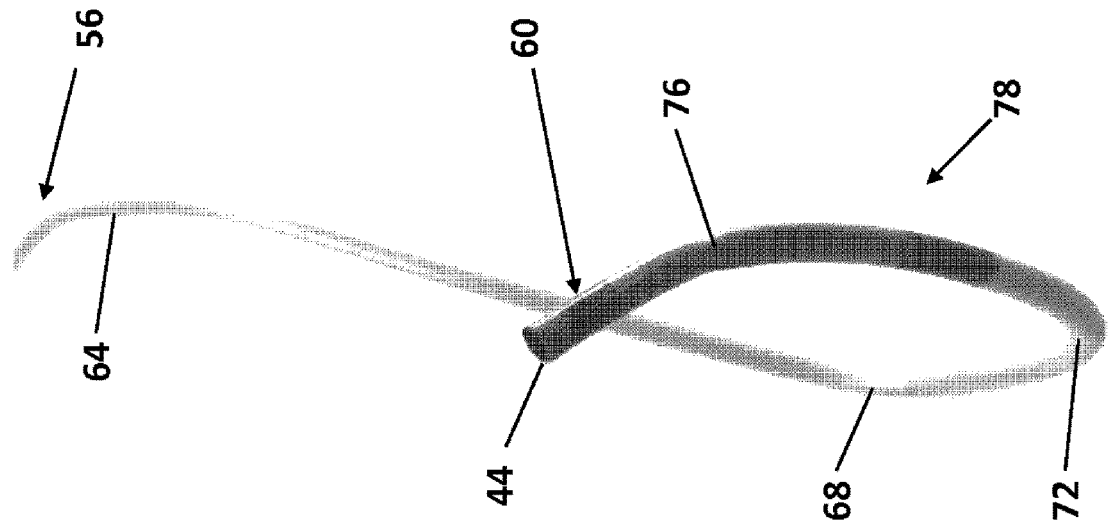
FIGS. 2A-2B are perspective views of a proximal side and distal side, respectively, of a curved section of a first configuration of an outer guide of the present apparatuses.
Figure 2B:
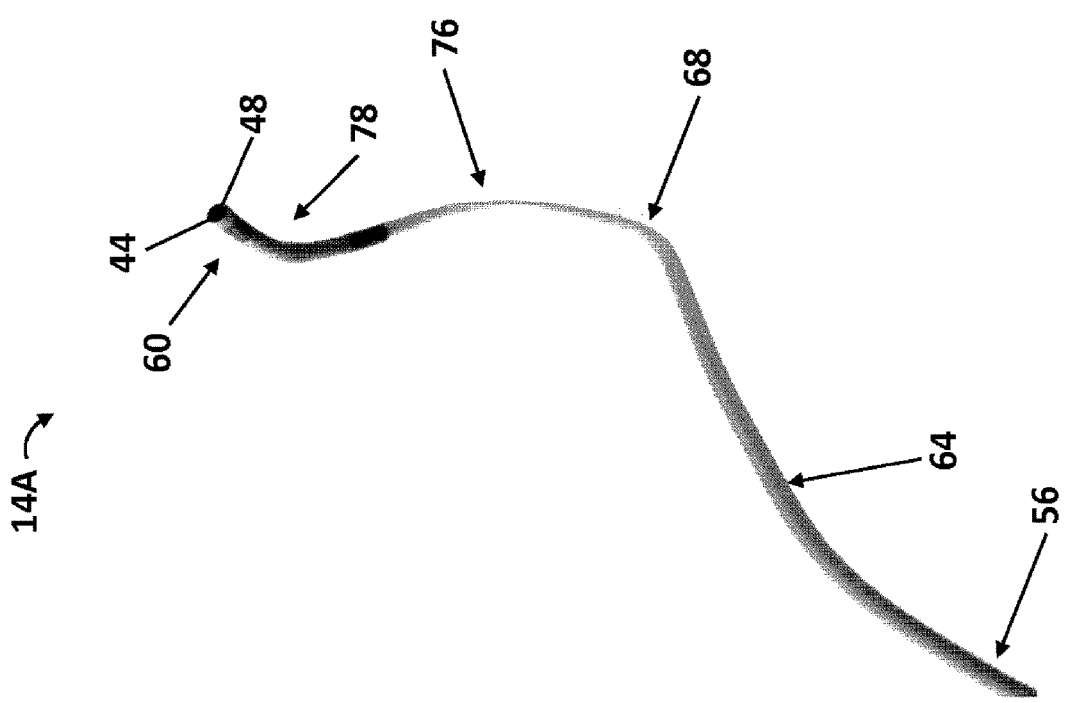

The configuration shown in FIGS. 2A and 2B shown therein and designated by the reference numeral 14A is a first configuration of outer sheath. In the depicted configurations, curved section 52 of outer sheath 14A may be shaped to facilitate easy access to LSA 26 or LIMA 12 from the preferred right transradial approach in a dependable and reproducible manner. As shown, a default shape of curved section 52 includes, from a proximal portion 56 of the curved section and extending toward a distal portion 60 of the curved section: a first curved segment 64; a second curved segment 68, a third curved segment 72, and a fourth curved segment 76. In this configuration, a portion of the outer sheath, viewed from the perspective of outer sheath distal end 44 facing toward outer sheath proximal end 40, may define a spiral 78 that curves in a counter-clockwise direction.

As shown in FIGS. 3A-4C, shown therein and designated by the reference numeral 14B is a second configuration of outer sheath. In this configuration, components of outer sheath 14B that are similar (e.g., in structure and/or function) to components discussed with reference to FIGS. 2A-2B and are labeled with the same reference numerals. As shown, outer sheath 14B may be shaped to facilitate easy access to LSA 26 or LIMA 12 from the preferred right transradial approach in a dependable and reproducible manner. For example, outer sheath 14B can include curved section 52 that comprises, from a proximal portion 56 of the curved section and extending toward a distal portion 60 of the curved section: a first curved segment 64; a second curved segment 68, a third curved segment 72, and a fourth curved segment 76.

Figure 3C:
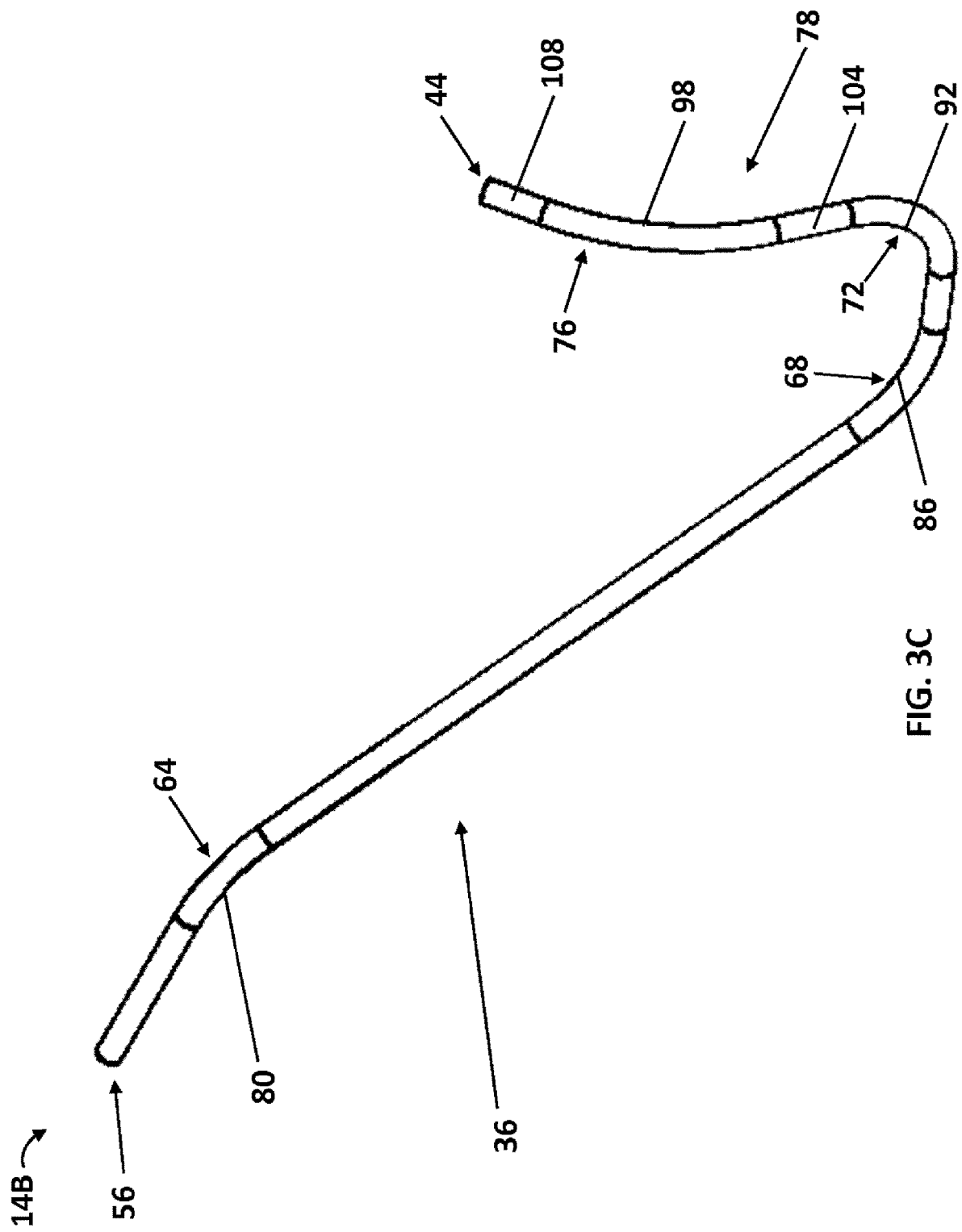
FIG. 3C is a perspective view of the curved section of the second configuration of the outer guide.

In the configuration shown in FIGS. 3A-3C, first curved segment 64 has a first curve 80 with a first radius of curvature 82 and second curved segment 68 has a second curve 86 having a second radius of curvature 88 where the curvature of the second curved segment is in a different direction than the curvature of first curve 80. For example, there may be an inflection point along curved section 52 at a point between first curved segment 64 and second curved segment 68 to avoid prolapse of outer sheath 14B into the ascending side of aortic arch 24 when navigating the outer sheath through RSA 22.

As shown, third curved segment 72 has a third curve 92 having a third radius of curvature 94 that is smaller than first radius of curvature 82 and/or second radius of curvature 88. For example, third radius of curvature 94 may be smaller than each of first radius of curvature 82 and second radius of curvature 88. In the depicted configurations, the curvature of the third curved segment in a common direction as the curvature of second curve 86. In the depicted configurations, fourth curved segment 76 has a fourth curve 98 having a fourth radius of curvature 100 that is larger than each of first radius of curvature 82 and second radius of curvature 88. In other configurations, fourth radius of curvature 100 may be smaller than first radius of curvature 82 or second radius of curvature 88. As shown, fourth radius of curvature 100 may be configured to enable outer sheath distal end 44 to engage LSA 26 from a right radial approach for various aortic geometries (e.g., type I, type II, and type III) without a loss of torque response.

As shown in FIG. 3C, a first extended segment 104 is disposed between third curved segment 72 and fourth curved segment 76, and a second extended segment 108 is disposed between fourth curved segment 98 and outer sheath distal end 44. In some configurations, spiral 78 of outer sheath 14B curves in a clockwise direction when viewed from the perspective of outer sheath distal end 44 facing toward outer sheath proximal end 40.

In some configurations, first extended segment 104 and/or second extended segment 108 are axial. For example (as illustrated in FIG. 4A), first extended segment 104 may extend along axis 140 and second extended segments 108 may extend along an axis 142 to form cylindrical members. Specifically, first and second extended segments 104, 108 may be circular cylinders. In other configurations, first extended segment 104 and/or second extended segment 108 may be curved with a radius of curvature that is larger than second radius of curvature 88. As shown in FIG. 4A, first extended segment 104 extends from a proximal end 116 to a distal end 118, where the proximal end abuts third curved segment 72 and the distal end abuts fourth curved segment 76. Second extended segment 108 extends from a proximal end 122 to a distal end 124, where the proximal end abuts fourth curved segment 76 and the distal end defines outer sheath distal end 44. Second extended segment 108 may extend laterally relative to at least a portion of third curved segment 72 and fourth curved segment 76.

In the configuration depicted in FIG. 4A, first extended segment 104 may be configured to provide a suitable distance between third curved segment 72 and fourth curved segment 76 such that outer sheath 14 may be shaped to navigate the tortuosity associated with the cardiac vasculature. Second extended segment 108 may be shaped to provide a suitable distance between fourth curved segment 76 and outer sheath distal end 44 to engage LSA 26 such that an orientation of outer sheath lumen 48 does not face the artery wall of the LSA. In some configurations, a third extended segment 112 is disposed between second curved segment 68 and third curved segment 72. In other configurations, second curved segment 68 and third curved segment 72 may be in contact with each other. Outer sheath 14B may comprise a plurality of extended segments that are disposed between curved segments (e.g., 64, 68, 72, 76) to enable efficient cannulation of LIMA 12.

Figure 4B:
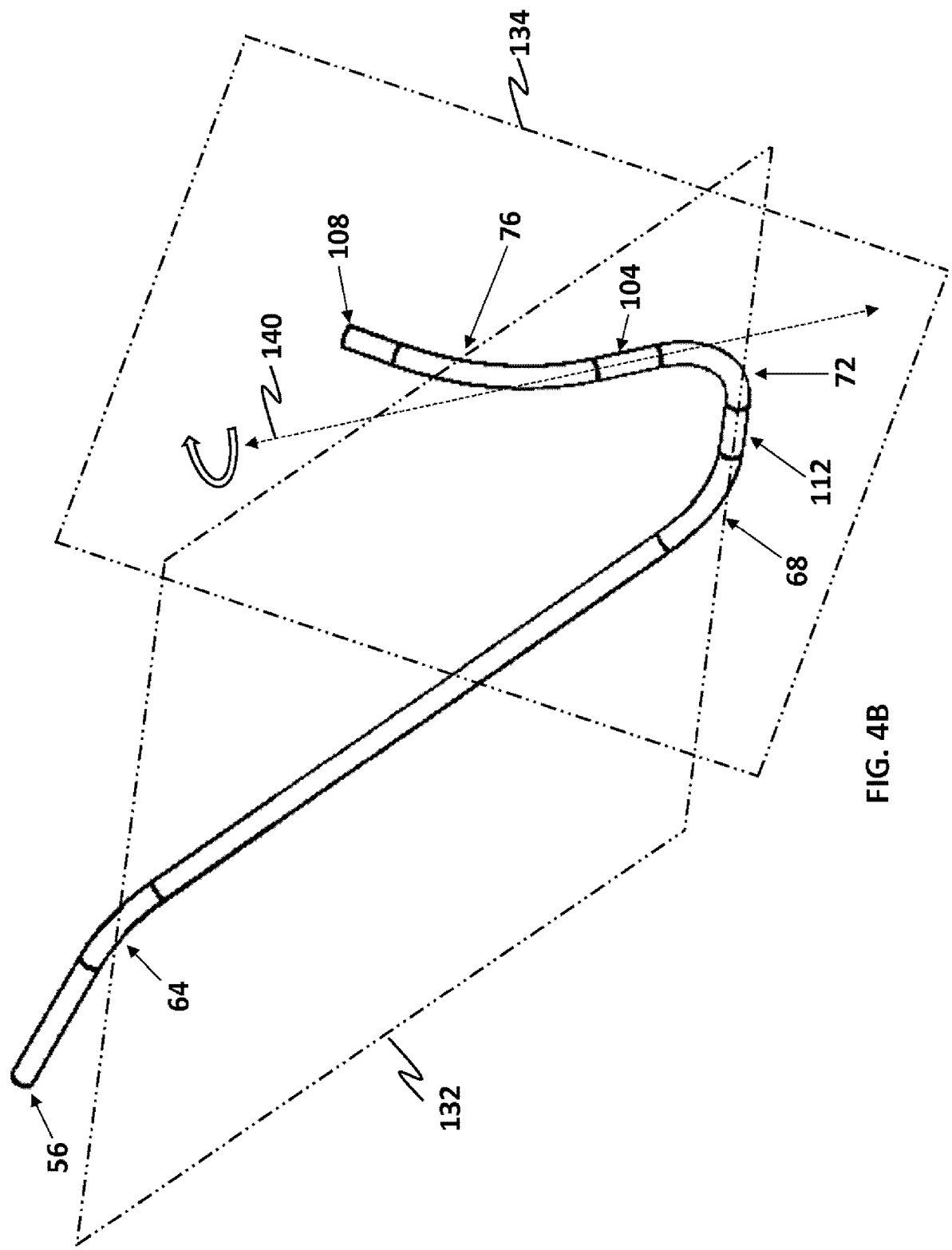

As shown in FIG. 4B, third curved segment 72 is disposed in a first plane 132, and fourth curved segment 76 is disposed in a second plane 134 that is rotated relative to the first plane around an axis 140 that extends through the center of outer sheath lumen 48 at proximal and distal ends 116, 118 of first extended segment 104. In some configurations, axis 140 may be disposed in first plane 132 and/or second plane 134. Second plane 134 may be rotated relative to first plane 132 around axis 140 by an amount equal to, or between any two of: 20, 30, 40, 50, 60, 70, 80, 90, 100, 110, 120, 130, 140, 150, 160, and/or 170 degrees. In some configurations, second extended segment 108 is disposed in second plane 134.

In the depicted configurations, second plane 134 is rotated relative to first plane 132 such that second extended segment 108 engages LSA 26 ostium with sufficient clearance between the artery wall. In this configuration second extended segment 108 may be coaxial with a portion of LSA 26. In some configurations, third curved segment 72 in first plane 132 is angularly disposed to fourth curved segment 76 in second plane 134. In this configuration, second plane 134 may be rotated relative to first plane 132 around axis 140 to deliver a greater range of motion to navigate through RSA 22 and aortic arch 26 without loss of torque response to properly cannulate the left subclavian artery.

In some configuration, first curved segment 64, second curved segment 68, third curved segment 72, and first extended segment 104, extend through first plane 132. In some configurations, first plane 132 bisects first curved segment 64, second curved segment 68, third curved segment 72, and first extended segment 104. In other configurations, first plane intersects a portion of third curved segment 72 at an acute or obtuse angle.

Figure 4E:
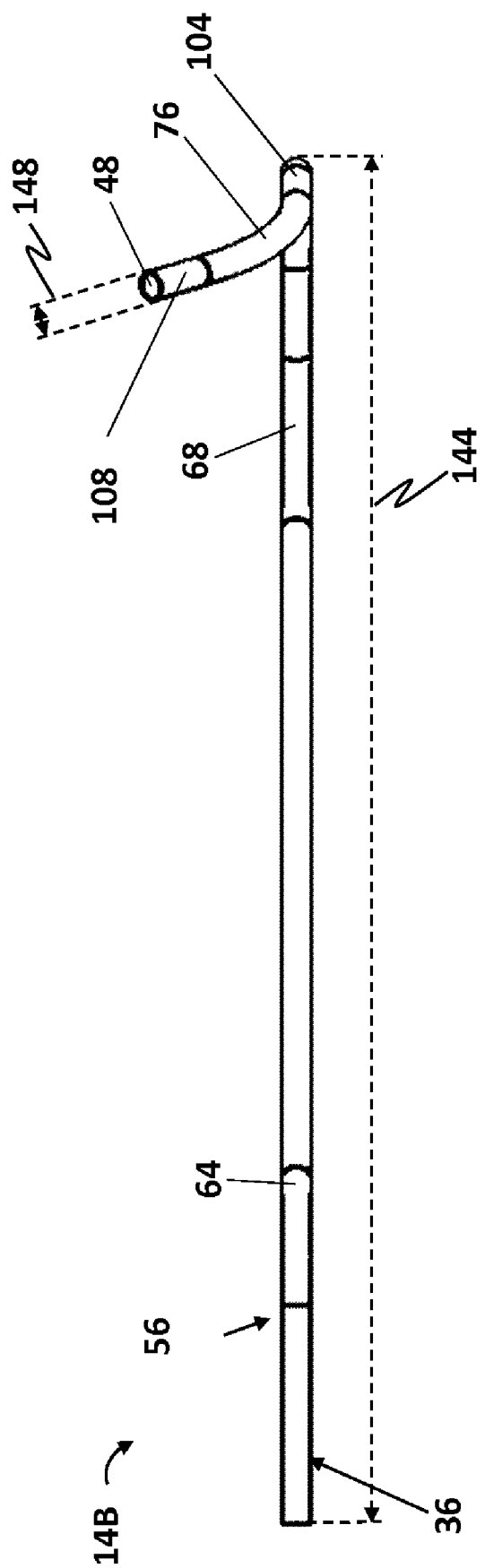
FIG. 4E is a top view of the curved section of the second outer configuration of the outer guide.

As shown in FIG. 4E, outer sheath 14 has a length 144 that extends between outer sheath proximal end 40 and outer sheath distal end 44. Length 144 may be less than or substantially equal to any one of, or between any two of: 45, 55, 65, 70, 75, 80, 85, 90, 95, 100, 105, 110, 115, 125, or 135 centimeters (cm). For example, length 144 is between 85 and 95 cm. More specifically, length 144 is between 85 and 90 cm. In some configuration, curved section 52 may be equal to any one of or between any two of: 30%, 40%, 50%, 60%, 70%, 80%, 90%, or 95% length 144 of the outer sheath 14.

In the configuration depicted in FIG. 4E, outer sheath 14 has an outer diameter 148 that is large enough to allow a separate catheter to pass through outer sheath lumen 48. Outer diameter 148 may be between 1 and 12 millimeters (mm). As shown, outer diameter 148 may correspond to any one of, or between any two of: 4, 5, 6, 7, 8, 9, 10, 12, 14, 16, 18, 20, 26, or 34 French gauge (FR). For example, outer diameter 148 may be 5, 6, or 7 FR. In some configurations, length 144 and outer diameter 148 of outer sheath 14 may allow for use of standard 100 cm, 5 FR catheters as inner sheath 18. In this configuration, outer sheath lumen 48 is shaped to allow for an operator to select from a range catheters to use with outer sheath 14, based on operator preferences or as required by specific anatomic scenarios.

Figure 5:
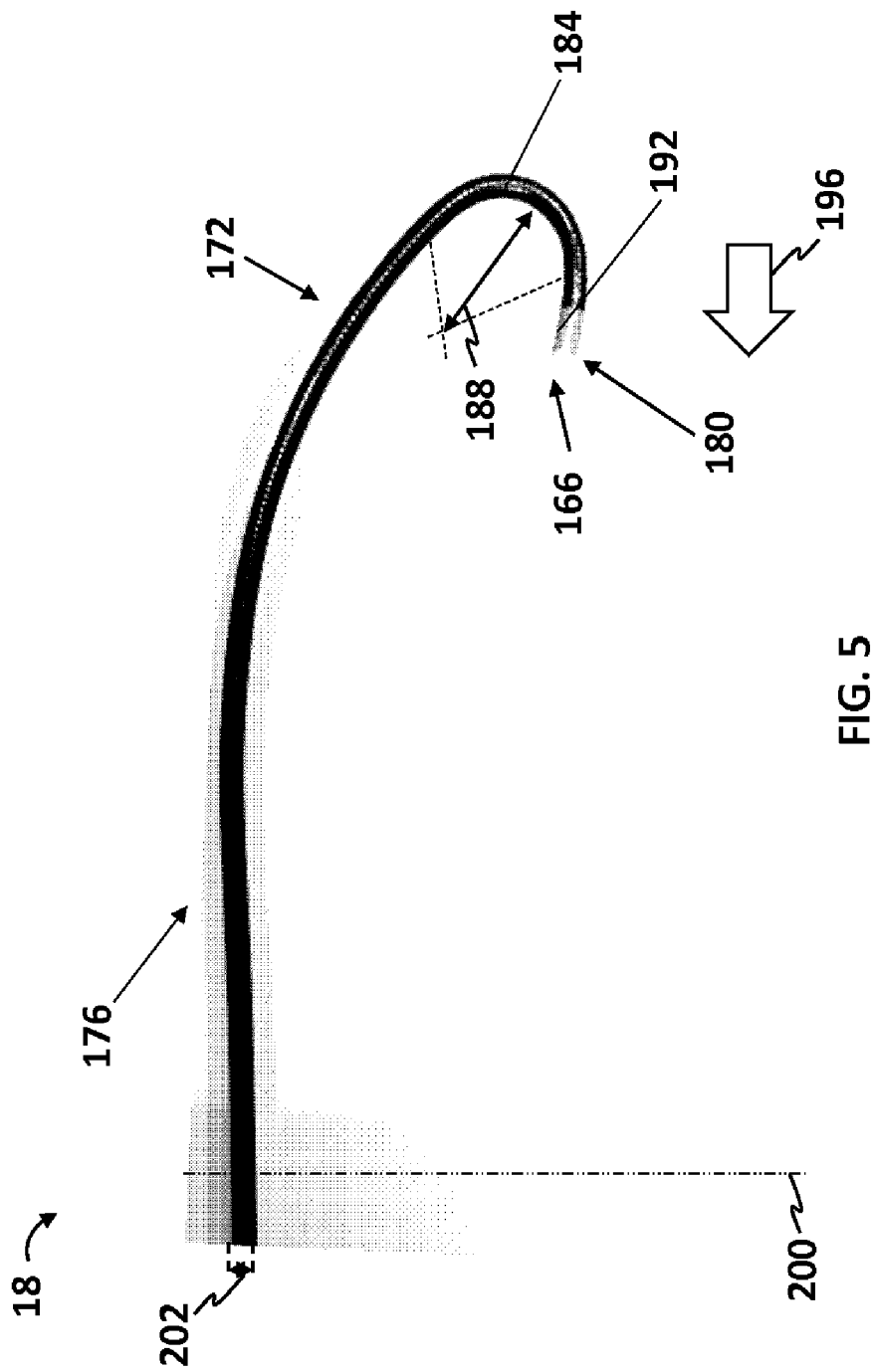
FIG. 5 is a perspective view of a distal portion of an inner guide of the present apparatuses.

As shown in FIG. 5, inner sheath 18 comprises a catheter designed to specifically facilitate a standard, uniform approach for cannulating LIMA 12 from a right transradial approach. In this configuration, inner sheath 18 comprises an elongated member 152 having an inner sheath body portion 156 that includes an inner sheath proximal end 160, an inner sheath distal end 164 opposite from the inner sheath proximal end, and an inner sheath lumen 168 extending through the inner sheath between the inner sheath proximal end and the inner sheath distal end.

In the depicted configuration, inner sheath comprises a curved section 172 that may be positioned nearer to inner sheath distal end 166 than to inner sheath proximal end 164. In other configurations, curved section 172 may comprise any segment of inner sheath body portion 160 between inner sheath distal end 166 and inner sheath proximal end 164. In other configurations, curved section 172 may correspond to a position between inner sheath distal end 166 and inner sheath proximal end 164 that is the same as a position of curved section 52 between outer sheath distal end 44 and outer sheath proximal end 40. In some configurations, curved section 172 of inner sheath 18 has a length that is greater than a length of curved section 52 of outer sheath 14.

In the configuration depicted in FIG. 5, curved section 172 includes, from proximal portion 176 of the curved section and extending toward a distal portion 180 of the curved section: a first curved segment 184 having a first radius of curvature 188 and a first extended segment 192 between the first curved segment and inner sheath distal end 166. As shown, first extended segment 192 has a curve with a radius of curvature that is larger than first radius of curvature 188 of curved segment 52. In other configurations, first extended segment 192 may be axial such that the first extended segment forms a substantially cylindrical shape.

As shown in FIG. 5, first curved segment 184 is of sufficient length relative to the first radius of curvature 188 that first extended segment 192 extends in a direction 196 toward a third plane 200. As shown, third plane 200 is intersected by and perpendicular to a portion of inner sheath 18. In some configurations, third plane 200 is intersected by a portion of inner sheath 18 that is closer to inner sheath proximal end 164 than to inner sheath distal end 166. In other configurations, third plane 200 may intersect a portion of inner sheath at an obtuse or acute angle. In some configurations, first curved segment 184 shaped into a soft 180 degree curve in order to conform to the downward/anterior origin of the LIMA.

In the configuration depicted in FIG. 5, inner sheath 18 has an outer diameter 202 that is small enough to fit within outer sheath lumen 48. Outer diameter 202 of inner sheath 18 may be between 0.5 and 8 millimeters (mm). As shown, outer diameter 202 of inner sheath 18 may correspond to any one of, or between any two of: 3, 4, 5, 6, 7, 8, 9, 10, 12, 14, 16, 18, 20, or 26 French gauge (FR). For example (as illustrated in FIG. 6A-6B), outer diameter 202 may be 3, 4 or 5 French gauge to allow for inner sheath 18 to telescope through outer sheath 14 via the Japanese "mother-daughter" guide technique to efficiently cannulate LIMA 12 without exchanging catheters.

In the depicted configuration, inner sheath 18 has a length 204 that is defined as the distance between inner sheath proximal end 164 and inner sheath distal end 166. As shown, length 204 of inner sheath 18 is greater than length 144 of the outer sheath lumen 14. Length 204 of inner sheath 18 may be substantially equal to any one of, or between any two of: 65, 70, 75, 80, 85, 90, 95, 100, 105, 110, 115, 125, 135, 145, 155, or 175 centimeters (cm). For example, length 204 may be between 95 and 105 cm.

Figure 6A:
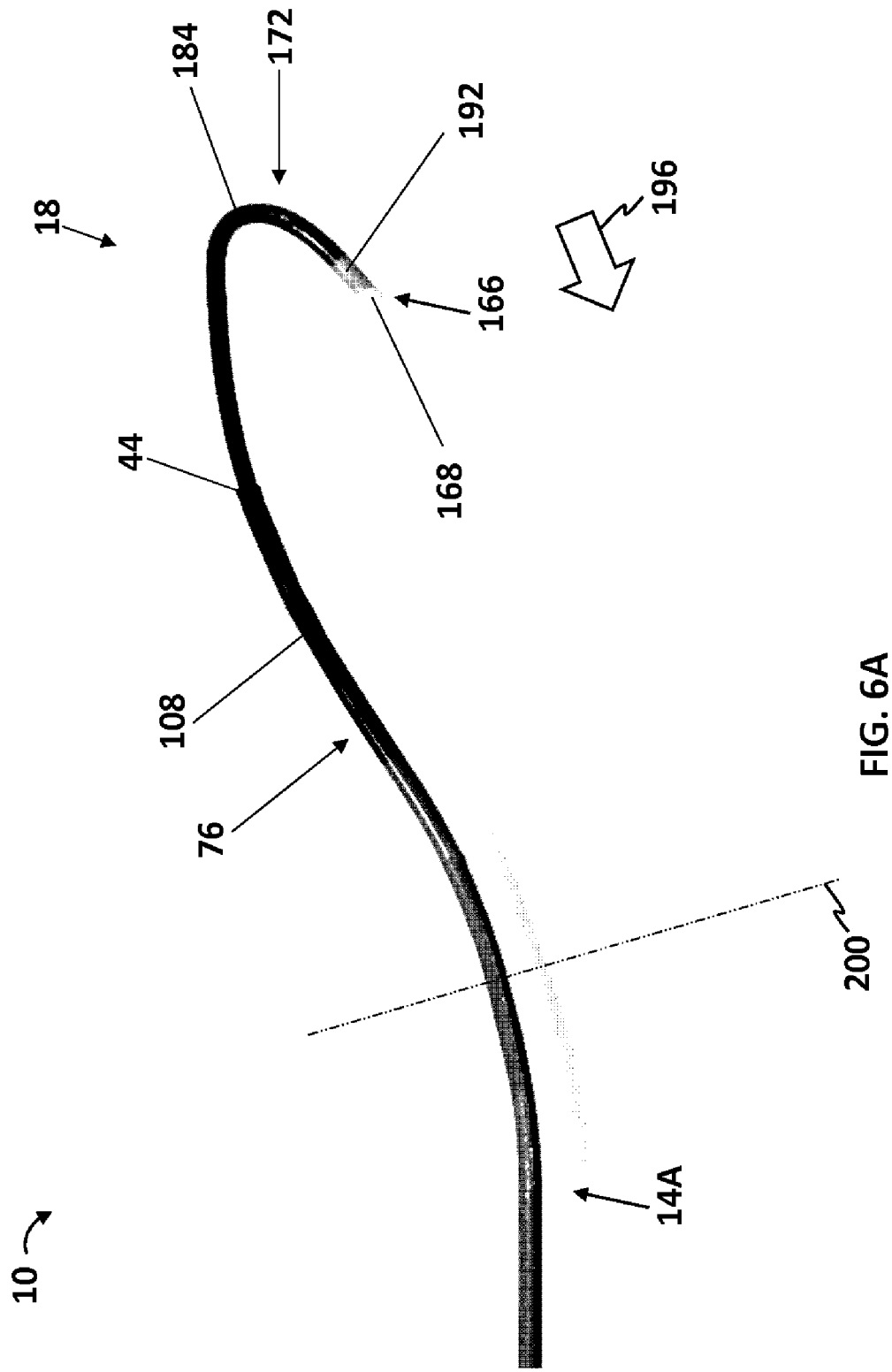
FIG. 6A is a perspective view of the first example of the present apparatuses including the first configuration of the outer guide.
Figure 6B:
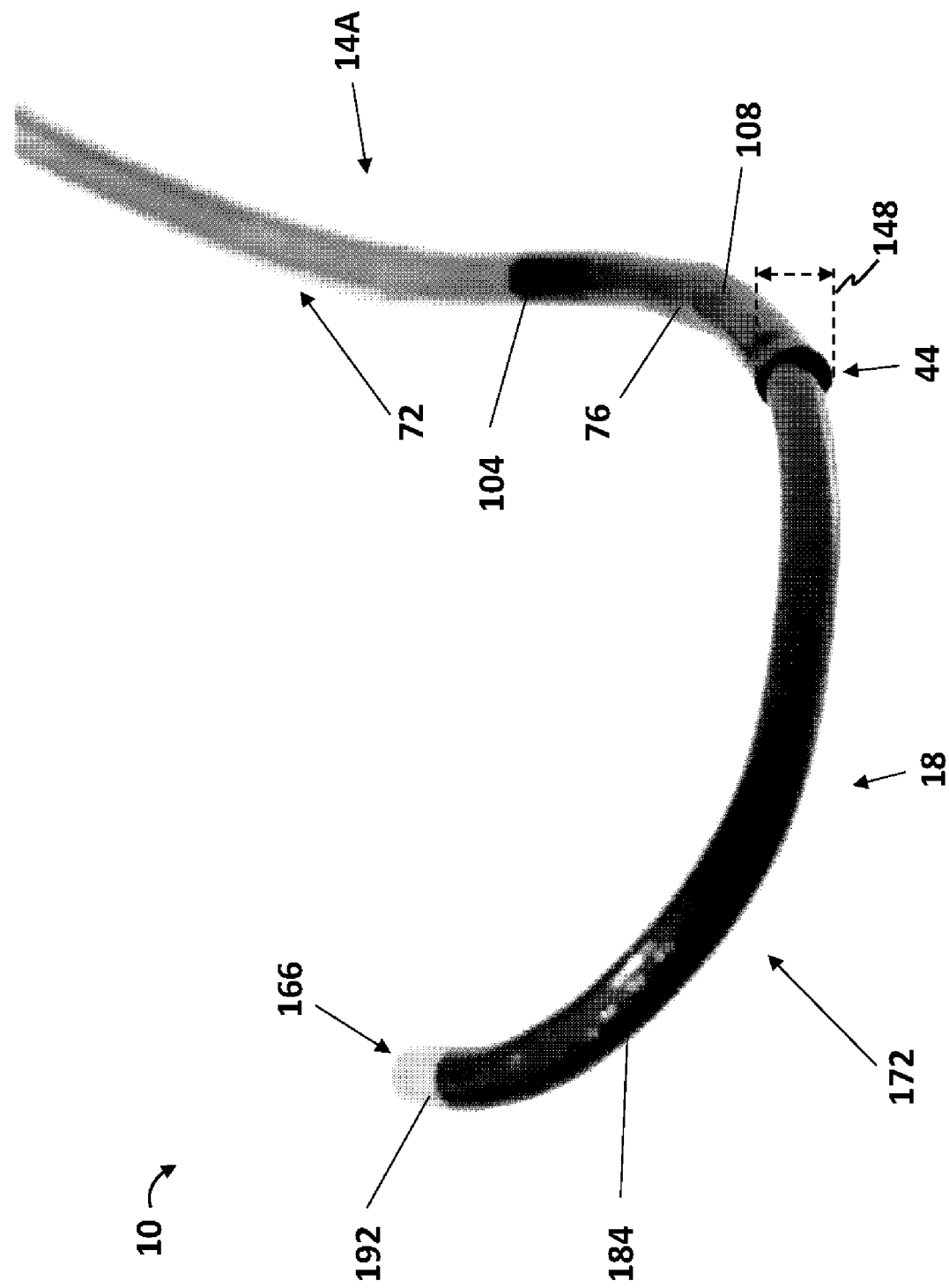
FIG. 6B is a distal view of the first example of the present apparatuses including the first configuration of the outer guide.

As shown in FIGS. 6A-6B, inner sheath 18 telescopes through outer sheath 14A. Although FIGS. 6A-6B show inner sheath 18 in operation with the first configuration of outer sheath 14A, it should be recognized that inner sheath 18 may operate similarly with the second configuration of outer sheath 14B. In the depicted configuration, at least a portion of curved section 172 of inner sheath 18 extends past distal end 44 of outer sheath. In the depicted configurations, inner sheath 18 is movable within outer sheath 14. In some configurations, a first portion of first curved segment 184 may be partially within outer sheath lumen 48, while a second portion of first curved segment is outside the outer sheath distal end 44. In other configurations, first curved segment 184 is completely outside of outer sheath lumen 48 when engaging LIMA 12.

As shown in FIG. 6A, first extended segment 192 of inner sheath 18 may extend in direction 196, which is opposite of a direction in which at least one of: first curved segment 64, second curved segment 68, third curved segment 72, fourth curved segment 76, first extended segment 104, and/or second extended segment extend. In some configurations, at least a portion of inner sheath 18 extends in the same direction as first extended segment 104, and one other portion of inner sheath extends in a direction opposite of first extended segment.

In the configuration depicted in FIG. 6B, inner sheath 18 is configured to have an outside diameter 202 that is smaller than outer diameter 148 of outer sheath 14 so inner sheath may extend through outer sheath lumen 48. In some configurations, inner sheath 18 extends through outer sheath lumen 48 from outer sheath proximal end 40 to outer sheath distal end 44 such that inner sheath distal end 166 may protrude from outer sheath 14 to engage LIMA 12. Outer sheath distal end 44 may be configured to be inserted into a blood vessel of a patient during an intravenous procedure to engage LSA 26 with sufficient space to allow inner sheath 18 to exit outer sheath lumen 48 without contacting the artery wall. In some embodiments outer sheath lumen 48 at distal end 44 is parallel with at least a portion of the artery wall of LSA 26.

The present methods for cannulating LSA 26 or LIMA 12 can include using any of the present mixing guide systems (e.g., 10), in any of the ways described above. Some methods, for example, comprise a step of inserting the outer sheath (e.g., 14A or 14B) into a blood vessel of a patient. For example, the blood vessel may comprise an artery or vein and specifically the blood steam may comprise a right radial artery of the patient.

Some methods comprise a step of navigating outer sheath (e.g., 14A or 14B) through RSA 22 into the descending aorta of aortic arch 24. In some methods, navigating outer sheath 14 comprises rotating curved section 52 using clockwise torque to line up second end segment 102 with LSA 26. In some methods, navigating outer sheath 14 comprises positioning second curved segment 68, third curved segment 72, and fourth curved segment 76 of outer sheath 14 into the descending aorta. Some methods further comprise positioning first curved segment 64 of outer sheath 14 in the right subclavian artery while the distal end 44 is disposed in LSA 26.

Some methods comprise a step of engaging LSA 26 ostium with distal end 44 of outer sheath 14. In some methods, distal end 44 of outer sheath 14 be advanced past the ostium of LSA and pulled back to engage the LSA. In some methods, distal end 44 of outer sheath 14 may be rotated so that second extended segment 102 is coaxial with a portion of LSA 26. For example, second extended segment 102 may be parallel with a portion of the artery wall of LSA 26 when distal end 44 is inserted into the LSA.

Some methods comprise a step of telescoping inner sheath 18 through lumen 48 of outer sheath 14 so that a portion of curved section 52 of inner sheath extends past distal end 44 of the outer sheath. In some methods, length 204 of inner sheath 18 is greater than a length 144 of outer sheath 10 so that inner sheath may extend through outer sheath lumen 48.

Some methods comprise engaging LIMA 12 with distal end 166 of inner sheath 18. In some methods, LIMA 12 is engaged without using a guidewire to exchange outer guide 14. Some methods comprise engaging LIMA 12 by advancing inner sheath 18 through LSA 26 past the ostium of the LIMA and providing counter-clockwise torque while pulling back on proximal end 164 of inner sheath 18 to engage LIMA ostium with distal end 166.

The above specification and examples provide a complete description of the structure and use of illustrative configurations. Although certain configurations have been described above with a certain degree of particularity, or with reference to one or more individual configurations, those skilled in the art could make numerous alterations to the disclosed configurations without departing from the scope of this invention. As such, the various illustrative configurations of the methods and systems are not intended to be limited to the particular forms disclosed. Rather, they include all modifications and alternatives falling within the scope of the claims, and configurations other than the one shown may include some or all of the features of the depicted configurations. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one configuration or may relate to several configurations. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A delivery system for accessing a blood vessel, the delivery system comprising:
   an outer sheath comprising an elongated member having an outer sheath body portion that includes an outer sheath proximal end, an outer sheath distal end opposite from the outer sheath proximal end, and an outer sheath lumen extending through the outer sheath between the outer sheath proximal end and the outer sheath distal end, the outer sheath including a curved section that is nearer the outer sheath distal end than the outer sheath proximal end;
   where a default shape of the curved section includes, from a proximal portion of the curved section and extending toward a distal portion of the curved section:
      a first curved segment having a first curve with a first radius of curvature;
      a second curved segment with a second curve having a second radius of curvature, the curvature of the second curved segment in a different direction than the curvature of the first curve;
      a third curved segment with a third curve having a third radius of curvature that is smaller than each of the first and second radii of curvature, the curvature of the third curved segment in a common direction as the curvature of the second curve;
      a fourth curved segment with a fourth curve having a fourth radius of curvature that is smaller than each of the first and second radii of curvature;
      a first extended segment between the third curved segment and the fourth curved segment, the first extended segment being axial or having a curve with a radius of curvature that is larger than the second radius of curvature; and
      a second extended segment between the fourth curved segment and the outer sheath distal end, the second extended segment being axial or having a curve with a radius of curvature that is larger than the second radius of curvature; and
   where the third curved segment is disposed in a first plane, and the fourth curved segment is disposed in a second plane that is rotated relative to the first plane around an axis that extends through the center of the outer sheath lumen at proximal and distal ends of the first extended segment.

2. The delivery system of claim 1, where the second extended segment extends laterally relative to the third and fourth curved segments.

3. The delivery system of claim 1, where a portion of the outer sheath, viewed from a perspective of the outer sheath distal end facing toward the outer sheath proximal end, defines a spiral that curves in a counter-clockwise direction.

4. The delivery system of claim 1, where the outer sheath has a length of between 85 and 95 centimeters (cm).

5. The delivery system of claim 1, where the outer sheath has a length greater than 85 centimeters (cm).

6. The delivery system of claim 1, where the outer sheath has an outer diameter corresponding to 6 French gauge or 5 French gauge.

7. The delivery system of claim 1, further comprising:
an inner sheath comprising an elongated member having an inner sheath body portion that includes an inner sheath proximal end, an inner sheath distal end opposite from the inner sheath proximal end, and an inner sheath lumen extending through the inner sheath between the inner sheath proximal end and the inner sheath distal end, the inner sheath including an inner curved section that is nearer the inner sheath distal end than the inner sheath proximal end;
where a default shape of the inner curved section includes, from a proximal portion of the inner curved section and extending toward a distal portion of the inner curved section:
a fifth curved segment having a fifth radius of curvature;
a third extended segment between the fifth curved segment and the inner sheath distal end, the third extended segment being axial or having a curve with a radius of curvature that is larger than the fifth radius of curvature;
where the fifth curved segment is of sufficient length relative to the fifth radius of curvature that the third extended segment extends in a direction toward a plane that is intersected by and perpendicular to a portion of the inner sheath that is closer to the inner sheath proximal end than to the inner sheath distal end; and
where the inner sheath is configured to extend through the outer sheath proximal end, the outer sheath lumen, and the outer sheath distal end.

8. The delivery system of claim 7, where the inner sheath has an outer diameter corresponding to 4 French gauge or 5 French gauge.

9. The delivery system of claim 7, where a length of the inner sheath is greater than a length of the outer sheath lumen.

10. The delivery system of claim 7, where the delivery system is configured to enable access to a patient's left internal mammary artery (LIMA) via a right transradial approach.

11. The delivery system of claim 1, where a portion of the outer sheath, viewed from a perspective of the outer sheath distal end facing toward the outer sheath proximal end, defines a spiral that curves in a clockwise direction.

12. A method for accessing the left internal mammary artery of a patient from a right transradial approach, the method comprising:
inserting a guide member into a blood vessel of a patient, the guide member comprising:
a curved section that includes, from a proximal portion of the curved section and extending toward a distal portion of the curved section:
a first curved segment having a first curve with a first radius of curvature;
a second curved segment with a second curve having a second radius of curvature, the curvature of the second curved segment in a different direction than the curvature of the first curve;
a third curved segment with a third curve having a third radius of curvature that is smaller than each of the first and second radii of curvature, the curvature of the third curved segment in a common direction as the curvature of the second curve;
a fourth curved segment with a fourth curve having a fourth radius of curvature that is smaller than each of the first and second radii of curvature;
a first extended segment between the third curved segment and the fourth curved segment, the first extended segment being axial; and
a second extended segment between the fourth curved segment and a guide member distal end, the second extended segment being axial; and
where the third curved segment is disposed in a first plane, and the fourth curved segment is disposed in a second plane that is rotated relative to the first plane around an axis that extends through the center of an outer sheath lumen at proximal and distal ends of the first extended segment;
navigating the guide member through the right subclavian artery into the descending aorta of the aortic arch;
engaging the left subclavian artery ostium with the distal end of the guide member;
telescoping an inner sheath through a lumen of the guide member; and
engaging the left internal mammary artery with a distal end of the inner sheath.

13. The method of claim 12, wherein inserting the guide member into a patient's blood vessel comprises inserting the outer sheath into the radial artery of the patient.

14. The method of claim 12 wherein the inner sheath comprises a curved section that includes:
a fifth curved segment having a fifth radius of curvature; and
a third extended segment between the fifth curved segment and an inner sheath distal end, the third extended segment being axial; and
where the fifth curved segment is of sufficient length relative to the first radius of curvature that the third extended segment extends in a direction toward a plane that is intersected by and perpendicular to a portion of the inner sheath that is closer to an inner sheath proximal end than to the inner sheath distal end.

15. The method of claim 13, wherein engaging the left subclavian artery ostium with a distal end of the guide member comprises rotating the distal end of the guide member so that the second extended segment is coaxial with a portion of the left subclavian artery.

16. The method of claim 15, wherein navigating the guide member comprises positioning:
positioning the second curved segment, the third curved segment, and the fourth curved segment of the guide member into the descending aorta; and
positioning the first curved segment of the guide member in the right subclavian artery.

17. The method of claim 12, wherein engaging the left internal mammary artery with a distal end of the inner sheath does not comprise using a guide wire to exchange the guide member.

* * * * *